United States Patent [19]
Burney et al.

[11] Patent Number: 6,056,700
[45] Date of Patent: May 2, 2000

[54] BIOPSY MARKER ASSEMBLY AND METHOD OF USE

[75] Inventors: Bryan T. Burney, Fishers; Michael E. Miller, Trafalgar; Joseph L. Mark, Indianpolis, all of Ind.

[73] Assignee: EMX, Inc., Franklin, Ind.

[21] Appl. No.: 09/170,610

[22] Filed: Oct. 13, 1998

[51] Int. Cl.⁷ ................................................. A61B 10/00
[52] U.S. Cl. .................... 600/564; 600/567; 606/167; 604/63
[58] Field of Search ..................... 600/562, 564, 600/566, 567; 606/167, 170, 181; 604/57, 46, 63, 73

[56] References Cited

U.S. PATENT DOCUMENTS

| | | | |
|---|---|---|---|
| 3,744,493 | 7/1973 | Booher et al. | 128/217 |
| 4,576,163 | 3/1986 | Bliss | 128/305 |
| 4,693,237 | 9/1987 | Hoffman et al. | 128/1 R |
| 4,776,346 | 10/1988 | Beraha et al. | 128/754 |
| 4,781,198 | 11/1988 | Kanabrocki | 128/654 |
| 5,034,005 | 7/1991 | Appling | 604/280 |
| 5,083,570 | 1/1992 | Mosby | 600/564 |
| 5,195,533 | 3/1993 | Chin et al. | 600/567 |
| 5,197,482 | 3/1993 | Rank et al. | 128/749 |
| 5,234,426 | 8/1993 | Rank et al. | 606/1 |
| 5,290,289 | 3/1994 | Sanders et al. | 606/61 |
| 5,487,392 | 1/1996 | Haaga | 600/566 |
| 5,538,010 | 7/1996 | Darr et al. | 128/754 |
| 5,562,613 | 10/1996 | Kaldany | 604/57 |
| 5,595,193 | 1/1997 | Walus et al. | 128/898 |

(List continued on next page.)

OTHER PUBLICATIONS

L. Liberman, MD, Excision with Biopsy Needle Leaves Residual Carcinoma, F–D–C Reports, Inc., p.2 (Dec. 15, 1997).

L. Liberman, MD et. al., "Clip Placement after Stereotactic Vacuum–assisted Breast Biopsy," Radiology, vol. 205 (No. 2), p. 6, (Nov. 4, 1997).

F. Burbank, MD and N. Forcier, MD, "Tissue Marking Clip for Stereotactic Breast Biopsy: Initial Placement Accuracy, Long–term Stability, and Usefulness as a Guide for Wire Localization," Radiology, vol. 205 (No. 2), p. 9, (Nov. 4, 1997).

S. Parker, MD and A. Klaus, MD, "Performing a Breast Biopsy with a Directional, Vacuum–assisted Biopsy Instrument," RSNA Refresher Courses, vol. 17 (No. 5), p. 20, (Oct. 4, 1997).

L. Solin MD et. al., "Determination of Depth for Electron Breast Boosts," Radiation Oncology Biol. Phys., Pergamon Journals Ltd. (USA), p. 6, (Dec. 4, 1987).

(List continued on next page.)

*Primary Examiner*—Max Hindenburg
*Assistant Examiner*—Charles Marmor, II
*Attorney, Agent, or Firm*—Baker & Daniels

[57] ABSTRACT

A biopsy-marking assembly for obtaining a biopsy sample from a biopsy site in a patient and marking the biopsy site is provided. The biopsy marking assembly includes a biopsy device and a marking element for marking the biopsy site. In preferred embodiments, the marking assembly is configured so that the marking element is deposited at the biopsy site before the tissue sample is taken. In some embodiments, the marker element is a V-shaped rod including two legs and a joint between the two legs. In some embodiments, the biopsy device includes an outer hollow needle defining a lumen therethrough and an inner needle slidingly engaged within the lumen. The inner needle defines a cavity for carrying the marker element for delivery to the biopsy site and for receiving a tissue sample. Methods are also provided for obtaining a biopsy sample and marking the biopsy site. The methods include loading a marker element into a biopsy device to obtain a biopsy-marker assembly, inserting the biopsy-marker assembly into a patient, depositing the marker element in the biopsy site and then obtaining a biopsy sample. In a preferred embodiment, the methods include rotating the biopsy device after depositing the marker element and before obtaining the biopsy sample.

21 Claims, 8 Drawing Sheets

U.S. PATENT DOCUMENTS

| | | | |
|---|---|---|---|
| 5,649,547 | 7/1997 | Ritchart et al. | 128/754 |
| 5,782,775 | 7/1998 | Milliman et al. | 600/567 |
| 5,800,445 | 9/1998 | Ratcliff et al. | 606/116 |
| 5,853,366 | 12/1998 | Dowlatshahi | 600/434 |
| 5,879,357 | 3/1999 | Heaton et al. | 600/567 |
| 5,902,310 | 5/1999 | Foerster et al. | 606/151 |

OTHER PUBLICATIONS

L. Fajardo, MD et. al., "Placement of Endovascular Embolization Microcoils to Localize the Site of Breast Lesions Removed at Stereotactic Core Biopsy," Radiology, p. 4, (Jan 4, 1998).

"Prostate Seeding Set and P.N.C.F. Prostate Seeding Set", P.N.C.F., Oct. 1995.

BIOPSY MARKER ASSEMBLY AND METHOD OF USE

FIELD OF INVENTION

The present invention relates generally to biopsy systems. Specifically, the invention concerns devices and methods for obtaining a biopsy sample and marking the site of the biopsy sample for later identification, repeat biopsy or surgical access.

BACKGROUND OF THE INVENTION

In the practice of diagnostic medicine, it is often necessary or desirable to perform a biopsy, or to sample selected tissue from a living patient for medical evaluation. Cytological and histological studies of the biopsy sample can then be performed as an aid to the diagnosis and treatment of disease. Biopsies can be useful in diagnosing and treating various forms of cancer, as well as other diseases in which a localized area of affected tissue can be identified.

Biopsy may be performed using an open or percutaneous technique. Open techniques are either excisional, removing the entire lesion, or incisional, removing a portion of the mass. Such techniques are expensive and traumatic. Therefore, the trend in recent years has been toward percutaneous procedures.

Percutaneous biopsy may be accomplished via fine needle aspiration or automated core biopsy. In fine needle aspiration, individual cells or clusters of cells are obtained through a hollow needle under suction for cytological examination. In core biopsy, a core or fragment of tissue is obtained for histological examination via a frozen section or paraffin section. Many automated devices are commercially available for obtaining a core needle biopsy sample. Both fine needle aspiration and core biopsy procedures are not generally excisional biopsy methods but in some cases the entire lesion is removed.

The chance of an excisional biopsy is increased using vacuum assisted core biopsy devices. Vacuum assisted biopsy methods obtain large specimens so use of this technique may result in an excisional biopsy, whether intentional or not. However, removal of all visible signs of a lesion on imaging examination does not guarantee complete histological excision of the lesion. (Fajardo, Laurie L., M.D. et al., "Placement of Endovascular Embolization Microcoils to Localize the Site of Breast Lesions Removed at Stereotactic Core Biopsy," *Radiology*, 1998, 206: 275–178.) Where the lesion is malignant, it can be difficult to locate the exact biopsy site at a later time. Also, the biopsy site may be difficult to locate for follow-up during the next several years if the lesion is benign or if additional sampling is required.

Whatever method is used, care is taken to minimize the physical trauma inflicted upon the intervening tissues that surround the affected area or target tissue. In fact, in recent years, biopsy technology has progressed to reduce the trauma associated with a biopsy so much so that the exact location of the biopsy site may not be easily located at a later time. For example, in the case of a breast biopsy, changes in the breast caused by a minimally invasive biopsy may be minimal in the first place and any changes that do occur may resolve quickly. Although this technology has provided many benefits to patients such as reduced scarring, tissue trauma, pain and cost, it aggravates the problem of later locating the exact biopsy site.

In response to this problem, Biopsys Medical Inc. has developed a product called MicroMark™ clip, which can be used to mark a breast biopsy site after vacuum-assisted biopsy if post-biopsy stereotactic images suggest that the lesion has been removed. (See, Parker, S H et al., "Performing a Breast Biopsy With a Directional . . .," *Radiographics*, September–October 1997, 17(5): 1233–52; Liberman, L et al., "Clip Placement after Stereotactic Vacuum-assisted Breast Biopsy," *Radiology* 1997, 205:417–422; Burbank, F and Forcier, N, Tissue Marking Clip for Stereotactic Breast Biopsy . . .," *Radiology* 1997, 205:407–415.) Using clips, the biopsy site can be easily located for treatment if the lesion is malignant or follow-up if it is deemed benign. Endovascular embolization microcoils have also been used as breast biopsy marker devices after biopsy as disclosed in Fajardo et al. Radiographically visible clips are also disclosed in Solin, L J et al., "Determination of Depth for Electron Breast Boosts," Int. J. Radiation Oncology Biol. Phys. 1987, 13:1915–1919.

The use of radiographically visible clips addresses the need to mark the location of a biopsy site for future reference, however it is difficult to deliver the clip to the biopsy site with precision. Currently, a clip is delivered with an introducer device after the biopsy sample is taken. However, inserting the clip after the biopsy presents some difficulties. When the biopsy sample is removed, the surrounding tissue will generally shift to fill the void from the sample. This is also aggravated if the tissue is dense, particularly in procedures in which the tissue is compressed. There is no guarantee that delivery to the exact location will be achieved with this approach.

It is generally recognized that precise placement of a localizing clip is difficult but necessary when the lesion is removed by vacuum assisted biopsy. Complex methods have been developed to calculate the distance of the clip from the intended location. For example, Burbank and Forcier (1997) disclose a "mask measurement system" to determine the distance that the clip is off-target. The system involves preparing a mask film from information transferred from two mammograms.

Precise placement of a localizing clip in combination with all types of biopsy methods may also be essential for further developments in the treatment of cancers, such as breast cancer. Liberman et al. (1997) suggest that improvements in the placement of markers may be required for the development of guiding therapies such as percutaneous ablative procedures. Accurate marker placement is also required for use as a target in wire localization surgeries as discussed by Burbank and Forcier.

Markers may also be beneficial in incisional biopsy procedures for many of the same reasons as for vacuum assisted biopsies that result in excision of the mass. Since most breast masses are deemed benign it would be useful to have a permanent marker at the biopsy site for follow up over a period of years. If patients are examined by a different radiologist or if records become unavailable, the marker would serve as a definitive locator of the site. The marker also may be used to confirm excision of the mass if the tissue is removed as part of a cancer therapy.

Therefore, a need remains for biopsy marking devices, delivery assemblies and methods that will increase the accuracy and reliability of biopsy site markers.

SUMMARY OF THE INVENTION

Briefly describing one aspect of the invention, a biopsy-marking assembly, for simultaneously obtaining a biopsy sample from a biopsy site in a patient and marking the biopsy site, is provided. The biopsy marking assembly includes cutting means for cutting tissue to obtain a tissue sample, receiving means for receiving a tissue sample and marking means for marking the biopsy site. In preferred embodiments, marking means is provided to automatically mark the biopsy site before the tissue sample is taken. In some embodiments, the receiving means includes a cavity both for receiving a tissue sample and for carrying the marking element for delivery to the biopsy site. In specific embodiments, the biopsy device includes an outer hollow needle defining a lumen therethrough and an inner needle defining the cavity for receiving a tissue sample slidingly engaged within the lumen. In some embodiments, the marker element is a V-shaped rod including two legs and a joint between the two legs. The rod can be compressed into a tissue sample cavity for delivery to a biopsy site.

The invention also includes methods for obtaining a biopsy sample and marking the biopsy site. The methods include loading a marker element into a biopsy device to obtain a biopsy-marker assembly, inserting the biopsy-marker assembly into a patient, depositing the marker element in the biopsy site and then obtaining a biopsy sample. In a preferred embodiment, the methods include rotating the biopsy device after depositing the marker element and before obtaining the biopsy sample.

Accordingly, it is one object of the invention to provide means for marking a biopsy site for later identification and access, if necessary. One benefit of this invention is that it provides devices, assemblies and methods for marking a biopsy site with precision. Another advantage of this invention is that devices of this invention overcome the pressure of dense tissue and resist migration after they are deposited in the tissue.

These and other objects, advantages and features are accomplished according to the devices and methods of the present invention.

DESCRIPTION OF THE PREFERRED EMBODIMENTS

Figure 1:
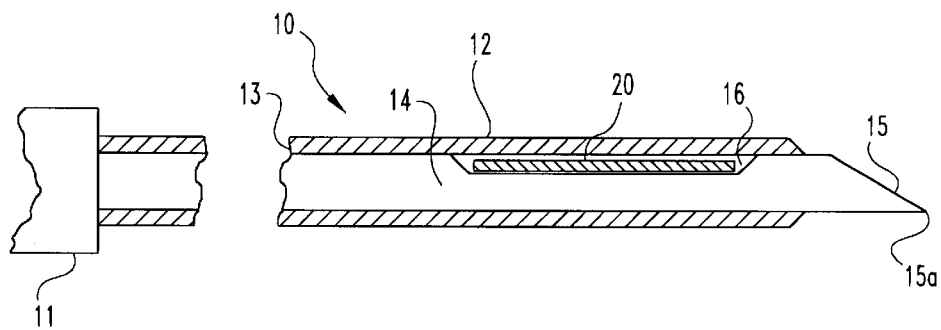
FIG. 1 is a partial side sectional view of a biopsy-marking assembly of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications of the illustrated devices and described methods and further applications of the principles of the invention which would normally occur to one skilled in the art to which the invention relates.

The present invention provides devices, assemblies and methods that precisely mark a biopsy site so that the site may be later located and accessed if necessary. The markers can be automatically delivered to the exact biopsy site during the biopsy procedure using the biopsy device. In the methods of this invention, the biopsy markers can be delivered at the same time as the biopsy sample is removed. Therefore, this invention solves the problem of attempting to locate the biopsy site after the biopsy device has been removed and tissue has shifted to fill the void left by the sample.

A biopsy-marking assembly 10 in accordance with a preferred embodiment of the invention is depicted in FIG. 1.

This embodiment includes a biopsy device 11 and a marker 20 of this invention loaded into a cavity 16 of device 11. Preferably, device 11 is a two piece biopsy needle as is commonly employed for obtaining tissue core specimens. The biopsy-marking device 11 depicted in FIG. 1 comprises an outer hollow needle 12 defining a lumen 13 therethrough. An inner needle 14 is slidingly engaged inside lumen 13 and is moveable relative to outer needle 12.

Figure 2:
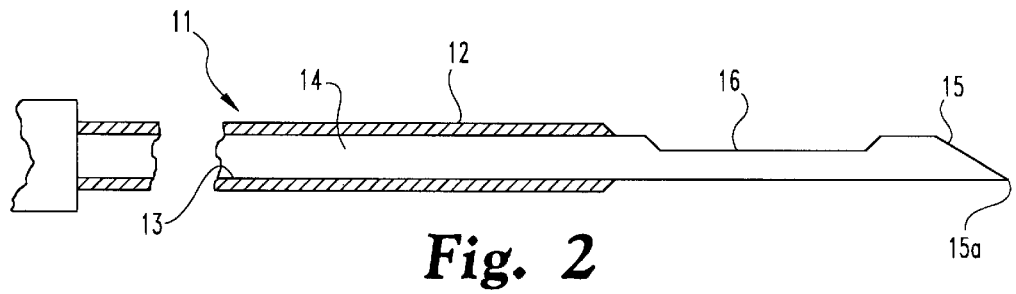
FIG. 2 is a side sectional view of a proximal end of a biopsy device.
Figure 3:
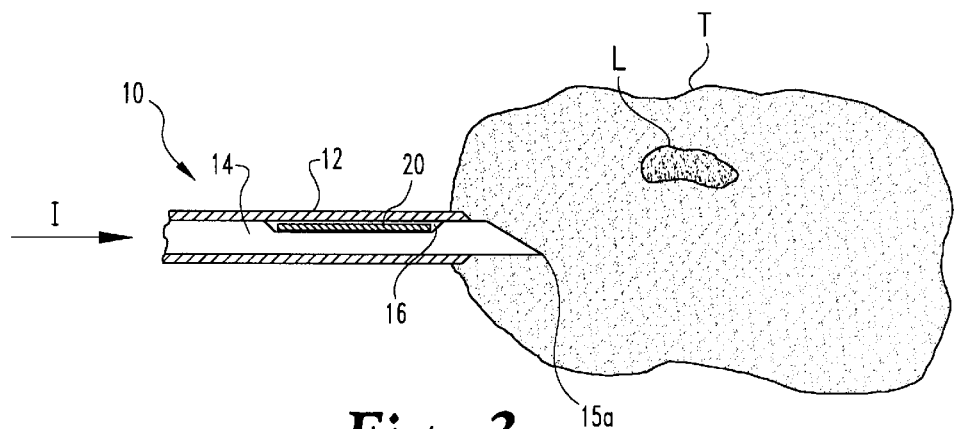
FIG. 3 is a side sectional view of the proximal end of a biopsy-marking assembly of this invention partially inserted into tissue.

The inner needle 14 defines a first end 15 having a tissue cutting point 15a and a cavity 16 adjacent first end 15 for receiving a tissue sample. The inner needle 14 is slidingly engaged within lumen 13. The inner needle 14 is slideable relative to outer needle 12 between a first position shown in FIG. 1 and a second position shown in FIG. 2. In the first position, inner needle 14 is retracted within lumen 13 so that outer needle 12 covers cavity 16. In the second position, the first end 15 of inner needle 14 is extended away from outer needle 12 to expose cavity 16 to tissue in the biopsy site. Biopsy device 11 also includes means for moving inner needle 14 and outer needle 12 with respect to each other. Such means are known in the art and commercially available. Biopsy devices of this type are available from U.S. Biopsy, Inc., a division of Promex, Inc. 3049 Hudson Street, Franklin, Ind., (317) 736-0128.

Biopsy-marking assembly 10 also includes marking means for marking the biopsy site immediately before or immediately after a biopsy sample is taken at the site. In a preferred embodiment shown in FIG. 1, marking means or marking element 20 is carried in cavity 16 when inner needle 14 is in the first position. Marking element 20 is deposited in tissue T when inner needle 14 is in the second position to expose cavity 16 and release marker 20.

A preferred method of this invention is depicted in FIGS. 3–6. In this method, the biopsy assembly 10 is inserted through a small incision or puncture made in the skin. The assembly 10 is then driven into the body in the direction of arrow I to approach lesion L of suspicion in tissue T. Tissue-cutting point 15A enters the tissue T and is positioned near the lesion L. During this insertion stage of the procedure, inner needle 14 is positioned within outer needle 12 in the first position. In this position, no more than proximal end 15 of inner needle 14 is exposed, cavity 16 is covered by outer needle 12 and a marking element 20 is contained within cavity 16.

Figure 4:
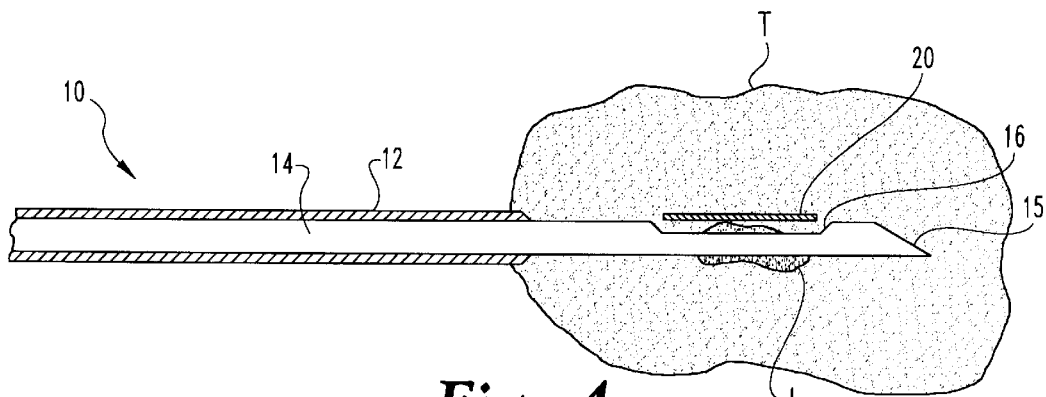
FIG. 4 is a side sectional view of the proximal end of a biopsy-marking assembly that has deposited a marker into tissue.

Referring now to FIG. 4, once assembly 10 has been positioned at the site for the biopsy, inner needle 14 is driven into tissue T far enough to expose cavity 16 of inner needle 14 and release marking element 20. After marking element 20 is released, soft body tissues will then prolapse into cavity 16. Of course, it is the aim of the surgeon to obtain lesion L tissue and so assembly 10 will be positioned so that lesion L will be trapped in cavity 16.

Figure 5:
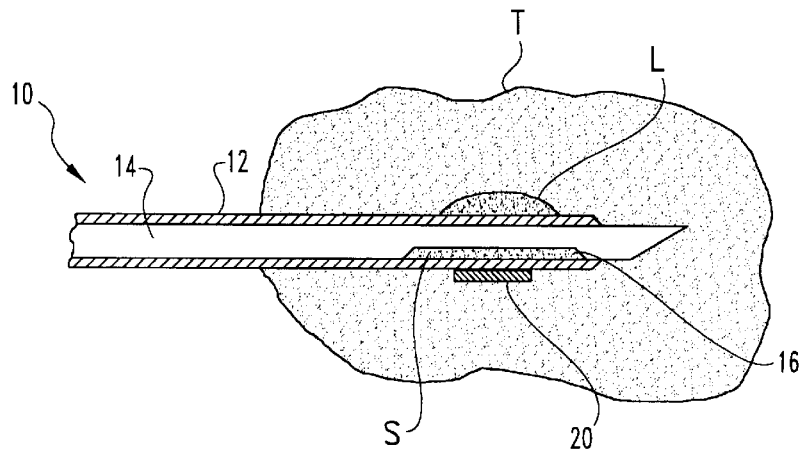
FIG. 5 is a side sectional view of the assembly of FIG. 4 showing the marker deposited in the tissue and a sample trapped within the cavity.
Figure 6:
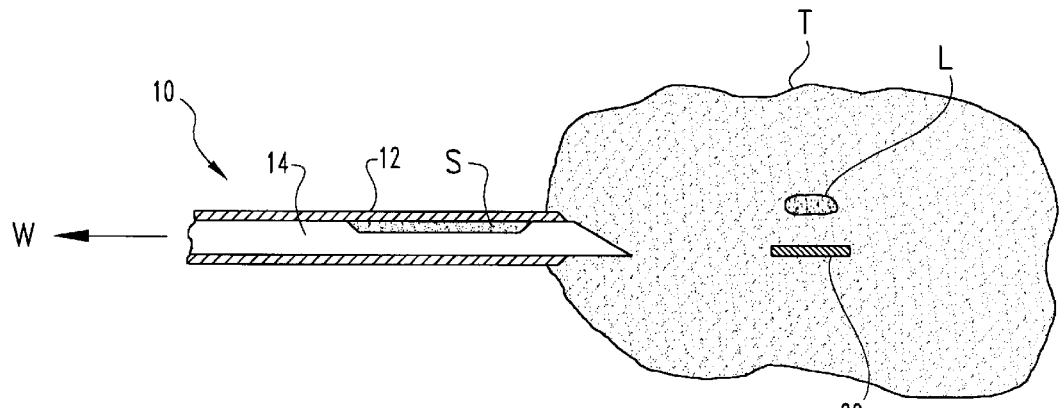
FIG. 6 is a view of the biopsy device withdrawing from the tissue with the marker deposited in the tissue and a sample trapped within the cavity.

Referring now to FIG. 5, outer needle 12 is then advanced along inner needle 14 in order to cover cavity 16. This forward movement of outer needle 12 severs the prolapsed tissue to obtain a tissue sample S, which becomes trapped in cavity 16 of inner needle 14. With outer needle 12 blocking the opening of cavity 16, biopsy assembly 10 may then be withdrawn carefully along arrow W shown in FIG. 6. Biopsy assembly 10 is then withdrawn from the target site carrying sample S in cavity 16 and leaving marker element 20 behind in tissue T. Thereafter, outer needle 12 is once again retracted to expose cavity 16 of inner needle 14, creating access to tissue sample S contained therein.

Preferably, multiple samples will be taken. At the surgeon's discretion, a marker may be left at the site as each sample is taken or only at the first and/or last sample site.

Figure 7:
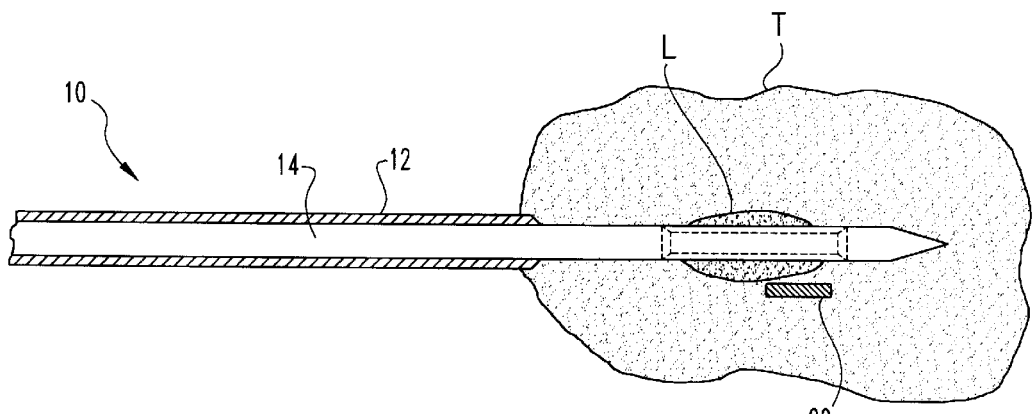
FIG. 7 is a side sectional view of the assembly of FIG. 4 with the inner needle rotated within the tissue.

In preferred embodiments, the invention includes means and steps for preventing the marker element from interfering with the prolapse of tissue into the cavity. In a preferred method depicted in FIGS. 4–5, the inner needle is rotated relative to the marker delivery site. As described above and shown in FIG. 4, biopsy marker assembly 10 is inserted into the tissue T so that proximal end 15 is adjacent the biopsy site or lesion L. Inner needle 14 is moved to deposit marker element 20 at the marker delivery site. Inner needle 14 is then preferably rotated as shown in FIG. 7 after depositing marker element 20 and before sliding outer needle 12 to capture the prolapsed tissue. Inner needle 14 alone or the entire biopsy needle assembly including both inner needle 14 and outer needle 12 may be rotated. The particular components of the biopsy device that are rotated are not critical so long as the cavity 16 is rotated away from the marker delivery site. In this way, marker element 20 will be clear of the action of outer needle 12 as it is actuated to trap the sample within cavity 16 as shown in FIG. 5. Preferably, the needle in the rotating step will have an angle of rotation that is between about 5° and about 180°. Most preferably, the angle of rotation would be less than about 90° and most preferably will be about 45°. Of course, the particular angle of rotation will be noted by the surgeon for precise location of the marker relative to the lesion L. The angle of rotation that is required will depend on the density of the tissue T and the shape, size, configuration and material of the marker element.

The marker elements of this invention will be of any suitable biocompatible material that can be visualized by a surgeon or radiologist using the visualization means of choice at the time, such as x-ray, ultrasound, stereotactic imaging and the like. For example, certain materials are highly visible under MRI, such as oil and Vitamin E, and certain surface features are better visualized using ultrasound technology. Such surface features include flats and angular features, etching and through-holes. In a preferred embodiment, marker element 20 is radiopaque. The material must be resistant to biodegradation for at least a suitable period of time. In most embodiments of this invention, it is contemplated that the material will not be biodegradable and will remain in the body for the life of the patient or until it is surgically removed. However, it is contemplated that in some applications it will be preferable that the material biodegrade after a suitable period of time after which the marker will no longer be needed, such as a number of years. In some embodiments, the markers are composed of medical grade stainless steel or titanium.

Figure 8:
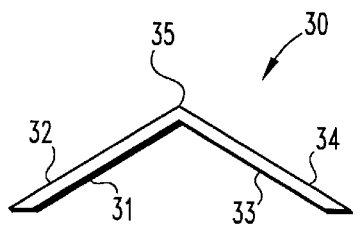
FIG. 8 is a side elevational view of one embodiment of a marker of this invention.

In the embodiments depicted in FIGS. 1–6, marking element 20 is a metal rod. The particular shape of the marking element will depend upon the application. For example, in breast tissue the marking element must overcome the force of the breast tissue, which will be weighted against the marker element as it attempts to escape from cavity 16. Therefore, in this instance, it may be preferable that the marking element be spring-loaded into cavity 16. In a preferred embodiment, the marker element is a rod 30 as shown in FIG. 8 that has an initial V-shaped position. Rod 30 includes a pair of legs 32, 34 and a joint 35 between legs 32, 34.

Figure 9:
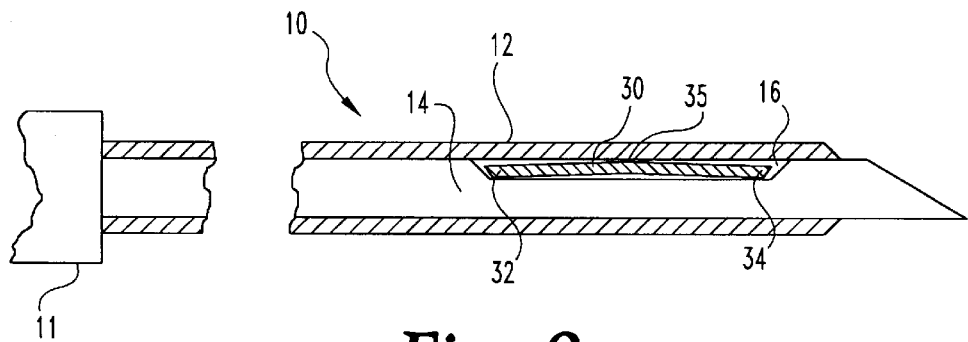
FIG. 9 is a partial side sectional view of a biopsy marking assembly of this invention including a marker of FIG. 8 compressed within the cavity.
Figure 10:
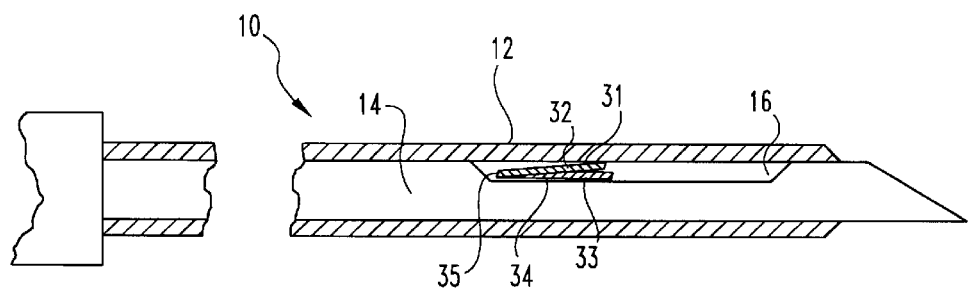
FIG. 10 is a partial side sectional view of a biopsy marking assembly of this invention including a marker of FIG. 8 folded within the cavity.
Figure 11:
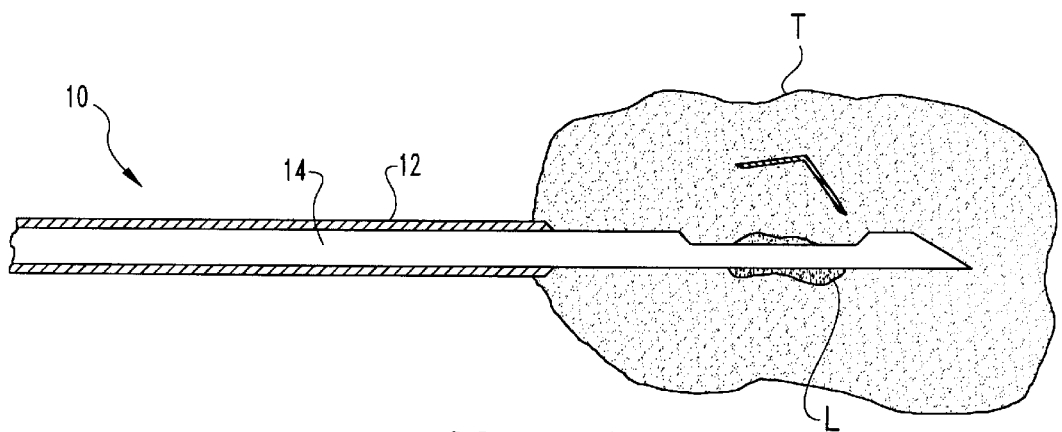
FIG. 11 is a partial side sectional view of a biopsy device within tissue with the marker of FIG. 8 released within the tissue.

In one embodiment, marker 30 is compressed in a flattened state as shown in FIG. 9. In another embodiment, shown in FIG. 10, marker 30 is compressed into a folded state with interior faces 31, 33 of legs 32, 34 pressed towards one another. In either configuration, when inner needle 14 is moved forward to expose cavity 16, marker element 30 will be released and will spring back to its initial V-shaped configuration as shown in FIG. 11. The material of choice for marker 30 will be one that is flexible enough so that it can be compressed into a spring-loaded state into the cavity and resilient enough to return to its preferred initial configuration. Preferred materials include stainless steel, titanium and radiopaque polymers or resins.

Figure 12:
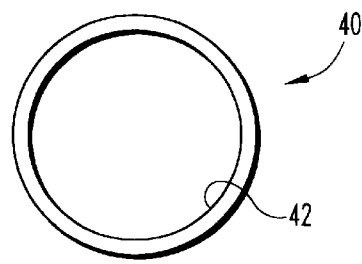
FIG. 12 is a side elevational view of another embodiment of a marker of this invention.
Figure 13:
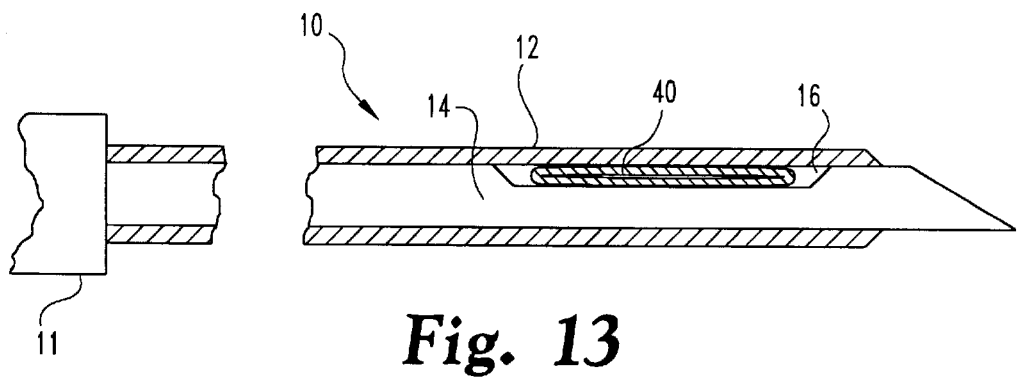
FIG. 13 is a side sectional view of the proximal end of a biopsy-marking assembly according to one embodiment of this invention including a marker of FIG. 12 compressed within the cavity.
Figure 14:
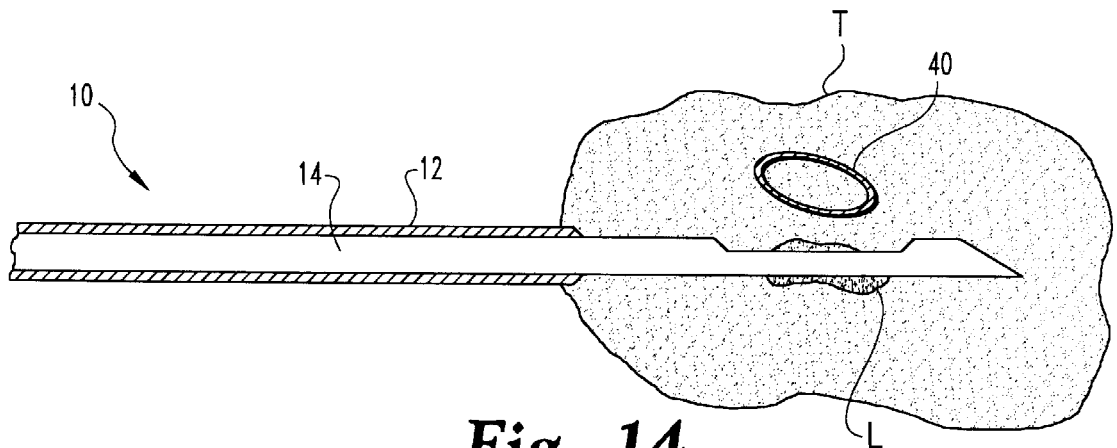
FIG. 14 is a partial side sectional view of the assembly of FIG. 13 inserted into tissue with the marker released in the tissue.

In another embodiment depicted in FIG. 12, marker element 40 is a metal rod formed into a continuous oval, such as a micro-coil. As shown in FIG. 13, a circular or oval marker is compressed within cavity 16 with interior wall 42 compressed towards itself for delivery to the biopsy site. As shown in FIG. 14, when biopsy device 10 is moved into the second position, marker 40 is spring released into the biopsy site.

Figure 16:
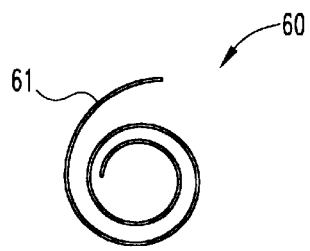
FIG. 16 is a side elevational view of another embodiment of a marker of this invention.
Figure 15:
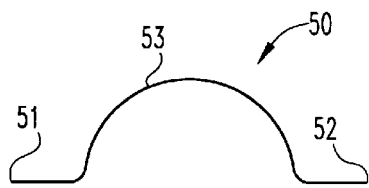
FIG. 15 is a side elevational view of another embodiment of a marker of this invention.
Figure 17:
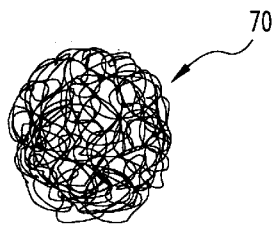
FIG. 17 is a side elevational view of another embodiment of a marker of this invention.

Any suitably shaped marker that can be spring-loaded into a chamber is contemplated. For example, FIG. 15 depicts a marker 50 having a pair of opposite ends 51 and 52 and a curved middle portion 53. The curved middle portion 53 forms a spring when marker 50 is compressed within a cavity. In another embodiment depicted in FIG. 16, marker 60 is a vertically coiled rod 61, which is compressible into a cavity for delivery to a biopsy site. Additional material can be used to coil the marker 70 into a "ball of string" structure as depicted in FIG. 17. Horizontally coiled rods are also contemplated, such as the marker 80 in FIG. 18. Marker 80 optionally includes an enlarged middle portion 81 and two opposite tapered ends 82, 83.

The invention contemplates any type of spring means that will allow the marker to be delivered to the biopsy site with sufficient force to overcome the force of the tissue against the marker. In one embodiment depicted in FIGS. 19–22, the marker 130 is a composed of a material that is responsive to a change in temperature to assume either an expanded shape or an altered configuration. One example of a material that is responsive to a change in temperature to assume a different shape or size is a shape memory alloy. Such alloys have a crystalline structure that can alternate between two phases depending on the temperature of the environment. In providing a shape memory alloy component, the component is first annealed to a specific shape by traditional means. The alloy is then heated to a temperature high enough that the crystalline structure assumes a phase known as the austenite phase. Next, the alloy is cooled until it reverts to a second phase called the martensite phase. Once in the martensite phase, the component may be deformed but the component will return to its original austenite phase shape when heated to a temperature above that at which the martensite phase returns to the austenite phase. Thus, after being deformed in the martensite phase, the alloy "remembers" its original annealed shape and will return to that original shape when heated above the austenite phase transition temperature. In doing so, the alloy converts heat energy into mechanical work.

The present invention exploits the shape memory material technology to provide markers that will be propelled from the cavity for delivery to the biopsy site. Marker 130 is composed of a shape memory alloy, preferably a nickel-titanium alloy and most preferably nitinol. The specific phase transitional temperature at which the phase transition occurs can be controlled by specifying the exact nickel to titanium ratio. In a preferred embodiment, the ratio is chosen to provide austenite transition temperature near body temperature, approximately 37° C. and a martensite transition temperature of about room temperature, approximately 25° C. However, the present invention contemplates other nickel-titanium ratios to provide desired austenite and martensite phase transition temperatures. The present invention further contemplates the use of other known shape memory alloys for use in constructing the markers of this invention. One example of such an alloy is an iron-based alloy including various percentages by weight of manganese, silicon and chromium.

Figure 19:
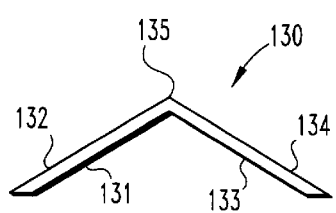
FIG. 19 is a side elevational view of a biopsy marker composed of a shape memory alloy and in the austenite phase.
Figure 20:
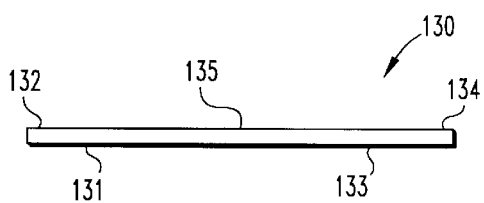
FIG. 20 is a side elevational view of the marker depicted in FIG. 19 in the martensite phase.
Figure 21:
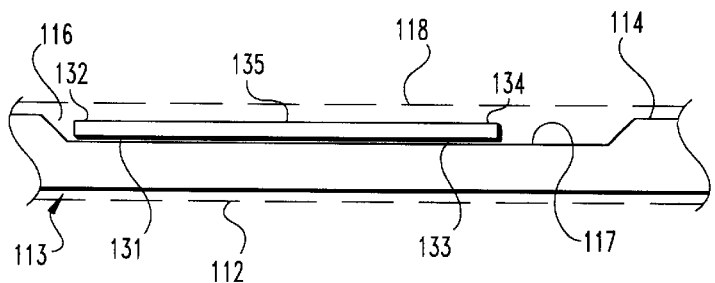
FIG. 21 is a partial side elevational view of a biopsy-marker assembly including the marker depicted in FIG. 20.
Figure 22:
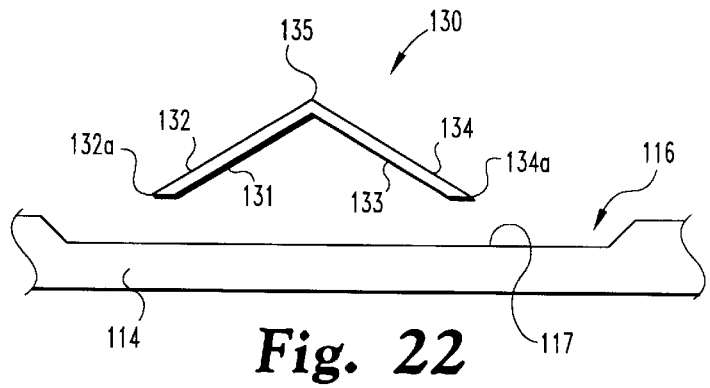
FIG. 22 is a side elevational view of the biopsy-marker assembly shown in FIG. 21 showing the marker in the austenite phase and expelled from the cavity.

According to a preferred approach in constructing marker 130, marker 130 is first annealed and contoured to a V-shape while in the austenite phase crystalline configuration as shown in FIG. 19. In this phase, marker 130 includes a pair of legs 132, 134 and a joint 135 between legs 132, 134. Interior faces 131, 133 of legs 132, 134 face one another. Marker 130 is then cooled until the martensite transformation occurs. While maintaining marker 130 below the shape transition temperature, marker 130 is deformed such that legs 132, 134 lie in a straight line or 180° from one another as shown in FIG. 20. In this configuration, marker 130 can be loaded into a cavity of a biopsy gun for delivery to the biopsy site. Preferably, marker 130 is loaded into a cavity with interior faces 131, 133 against bed 117 of cavity 116 and opposite opening or mouth 118 of cavity 116 as depicted in FIG. 21. When inner needle 114 is extended from lumen 113 of outer needle 112 and cavity 116 is exposed to tissue, marker 130 is heated to body temperature, which is sufficient to transform the alloy to the austenite phase configuration. In doing so, marker 130 "remembers" its original configuration, and its returns to its initial V shape. When marker 130 is heated, ends 132a, 134a of legs 132, 134 will be drawn together and push against bed 117 of cavity 116 to be expelled from cavity 116 as shown in FIG. 22. In some embodiments, additional heating means as are known in the art are used.

Figure 23:
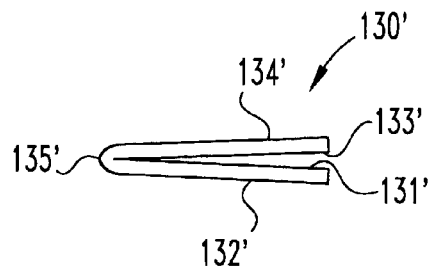
FIG. 23 is a side elevational view of another embodiment of a shape memory marker in the martensite phase.
Figure 24:
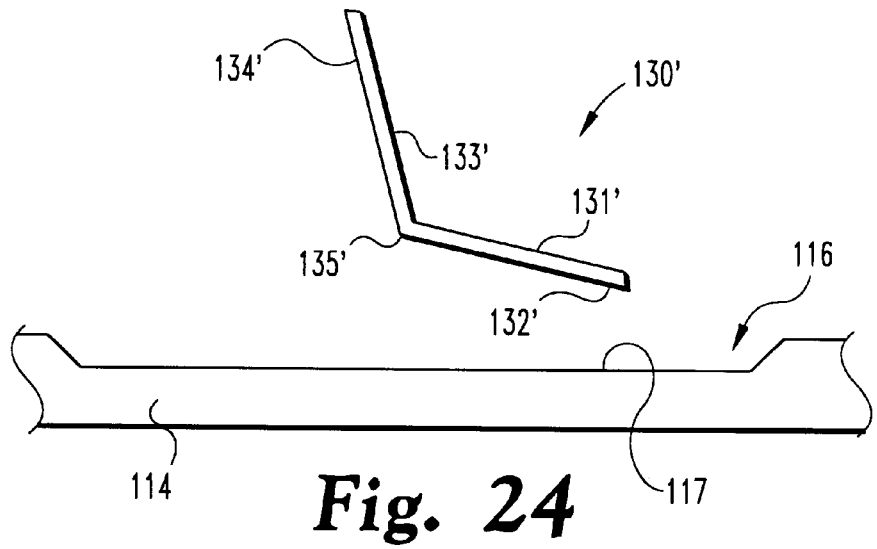
FIG. 24 is a side elevational view of a biopsy-marker assembly showing the marker of FIG. 23 in the austenite phase and expelled from the cavity.

In other embodiments, the marker is annealed and contoured to a V-shape as described above and shown in FIG. 19. After the marker is cooled to the martensite phase, marker 130' is deformed to be folded at joint 135' with interior faces 131', 133' of legs 132', 134' pressed towards one another as shown in FIG. 23. The folded marker 130' can be loaded into a cavity as shown for marker 30 in FIG. 10. When inner needle 114 is extended from lumen 113 of outer needle 112 and cavity 116 is exposed to tissue, marker 130' is heated to body temperature. Referring now to FIG. 24, as marker 130' "remembers" its original configuration and returns to its initial V shape, the mechanical action of leg 132' against cavity bed 117 ejects marker 130' from cavity 116.

The preferred phase transition temperatures are approximately room temperature and body temperature for ease of handling. Where other alloys are used which have different phase temperatures, the markers will be treated to achieve those temperatures.

Figure 25:
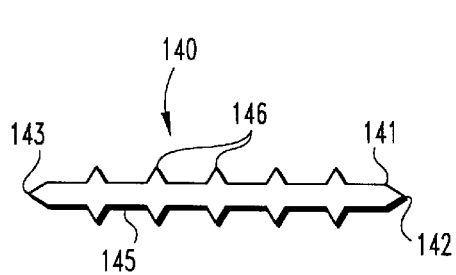
FIG. 25 is a side elevational view of another embodiment of a marker of this invention.
Figure 18:
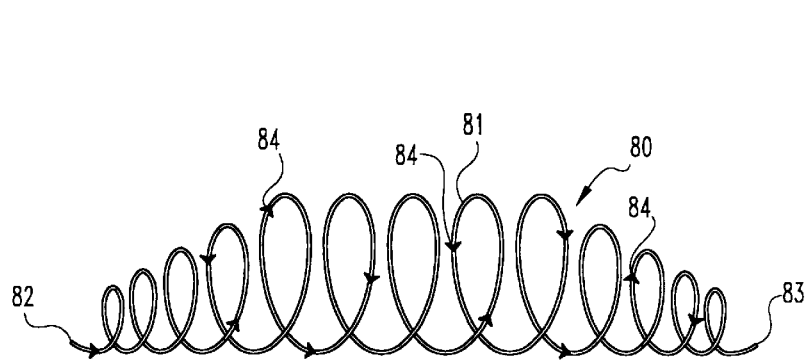
FIG. 18 is a side elevational view of another embodiment of a marker of this invention.

In some applications, it is desirable that the marker element include stabilization means for grasping tissue to prevent or retard migration of the marker within the tissue. For example, marker element 140 depicted in FIG. 25 includes a rod 141 defining two sharpened opposite ends 142, 143. Along its length, rod 141 is provided with sharpened surface projections 146 in between flattened valley area 145. Other stabilization means include barbs 84 depicted in FIG. 18. Although barbs 84 and surface projections 146 are depicted in FIGS. 18 and 25 as an example, these features may be provided on any of the markers of this invention. Also, any suitable stabilization means is contemplated by this invention. The stabilization means will be formed into the marker how ever is appropriate for the materials, such as by molding or machining.

The invention contemplates markers of any suitable size and shape. The markers of this invention will be sized and shaped large enough to be visualized yet compact enough to be delivered to the biopsy site in the cavity of a biopsy needle. Preferably, the marker will have a dimension of at least about 1 mm and no more than about 30 mm for applications such as breast. In one specific embodiment, the marker has a length of 0.6 inches (15 mm) and a width of 0.38 inches (9.5 mm) and is composed of titanium.

Although specific examples are provided of markers and biopsy-marker assemblies as well as methods for marking a biopsy site, these examples are merely representative of embodiments of the present invention. Any suitable biopsy device is contemplated which includes means for obtaining a tissue sample, cutting means for cutting tissue and marking means for marking the biopsy site. In preferred embodiments, marking means is provided for marking the biopsy site before a biopsy sample is taken. In other preferred embodiments, the marking element is contained within a cavity in a biopsy device element for delivery to the biopsy site. In some embodiments, the biopsy device means is a single action biopsy device as is known in the art.

Figure 26:
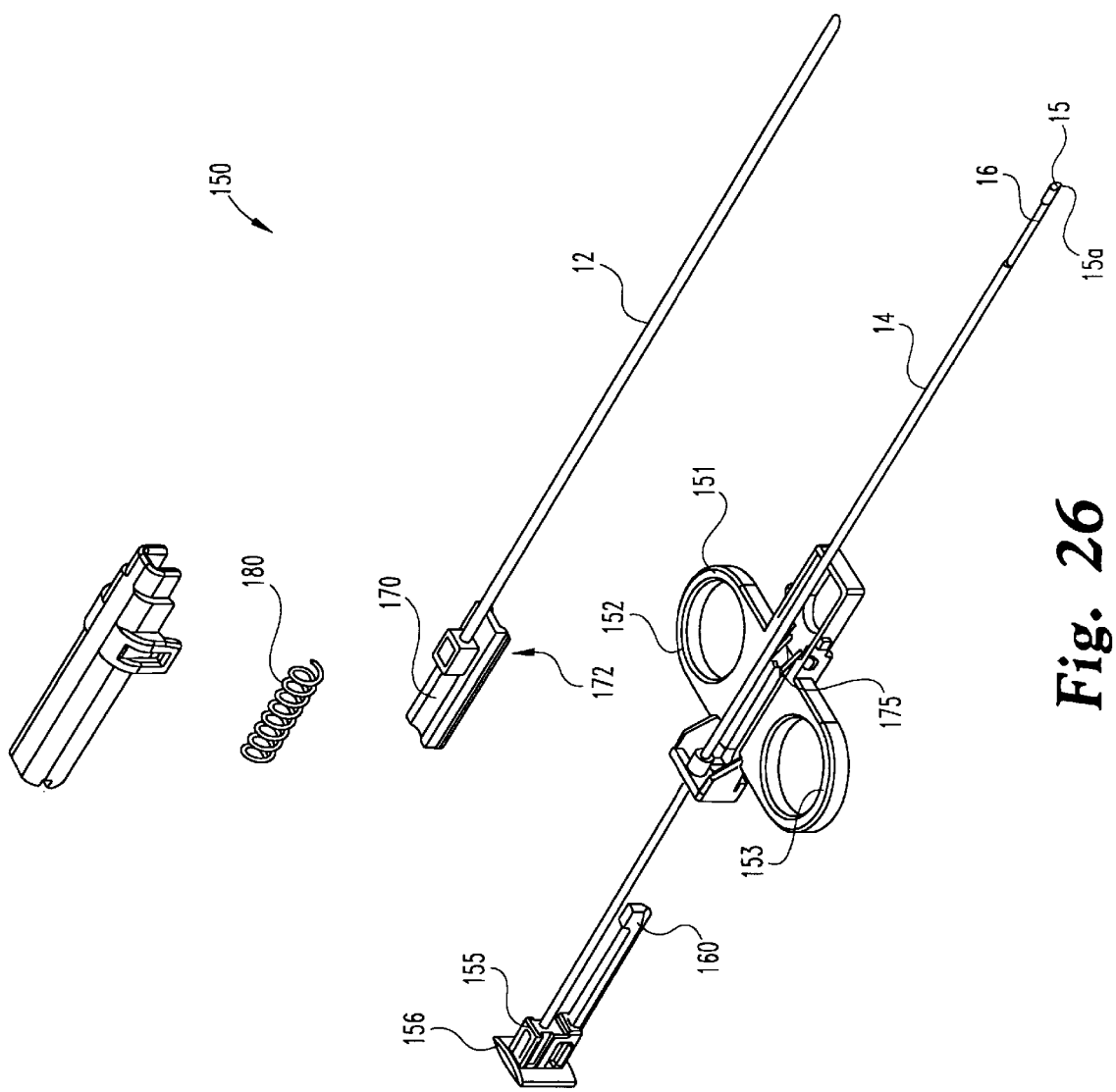
FIG. 26 is an exploded view of a biopsy-marking assembly according to one embodiment of this invention.

A single action biopsy device which can be used with this invention is manufactured and marketed by U.S. Biopsy, Inc., a division of Promex, Inc. 3049 Hudson Street, Franklin, Ind. 46131 (317) 736-0128), and is depicted in FIG. 26. Device 150 includes a housing 151 having finger grips 152 and 153. An actuator 155 is operatively engaged to both the inner needle 14 and the outer needle 12. The actuator includes a gripping portion 156 and a drive mechanism 160. The drive mechanism 160 operates to depress a drive carriage 170 against the action of a spring 180. The housing 151 includes a resilient latch 175 that engages the underside 172 of the carriage 170 in the retracted position. The latch 175 is released by forward movement of the drive mechanism 160 so that the spring 180 pushes the carriage 170 outwardly to expose the cavity 16 of the inner needle 14. Further movement propels the outer needle 12 over the inner needle 14 to trap tissue within the cavity. The operational relationship between the outer needle 12 and the inner needle 14 is described above and depicted in FIGS. 1–6. A single action biopsy device of this type is preferred because it allows rotation of inner needle 14 between the steps of releasing the marker element and obtaining a biopsy sample. This allows the biopsy marker to be ejected clear from the cavity to expose the cavity to the lesion L.

Although single action biopsy devices are preferred in this invention, double action biopsy devices, such as the device disclosed in U.S. Pat. No. 5,538,010 to Darr and Ireland, may also be used. The needle assembly is sequentially driven by a spring loaded drive mechanism. The device may be inserted into tissue in the first position as described above. When the device is actuated, the inner needle fires to expose the cavity, and the outer needle is immediately fired upon the firing of the inner needle to trap the tissue sample within the cavity. The marker element could be delivered in the cavity of such device, but the immediate firing of the outer needle may not provide enough time for the marker element to clear the cavity. However, such double-action biopsy devices could be modified to address this. For example, the firing of the outer needle could be delayed to allow sufficient time for the marker element to clear the cavity area or to allow rotation of the inner needle before the outer needle covers the cavity to trap the sample within the cavity.

Figure 27:
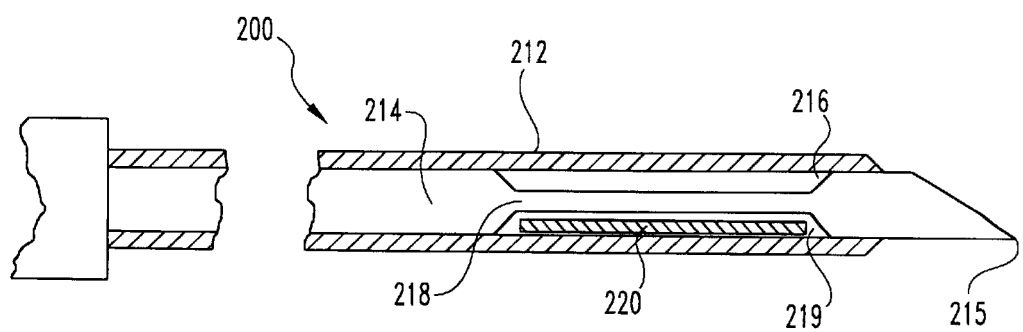
FIG. 27 is a partial side sectional view of a biopsy marking assembly having a marker chamber separate from the tissue sample cavity.

Another modification is depicted in FIG. 27. A double-action biopsy-marker assembly 200 is provided with an outer needle 212 and an inner needle 214. Inner needle 214 defines a sample cavity 216 as described above. Inner needle 214 also defines a separate and oppositely located marker chamber 219. A wall 218 of inner needle 214 separates marker chamber 219 and sample cavity 216. In this embodiment, marker element 220 is automatically ejected from marker chamber 219 and delivered approximately 180° from the biopsy sample site. Marker chamber 219, of course, may be defined in other locations in inner needle 214. For example, marker chamber 219 could be between proximal end 215 and sample cavity 216 so that the marker will be placed slightly deeper than the biopsy sample site. Marker chamber 219 could also be placed between sample cavity 216 and the distal end (not shown). Any configuration is contemplated so long as marker chamber 219 will be exposed when inner needle 214 is moved from the first position to the second position.

In some embodiments where multiple marker placements are desirable, means can be provided to incrementally feed a length of marker material through a hole defined in the outer needle 212. The material can be urged out the hole with a ramp built within the marker chamber 219. Discrete markers can be severed and left in the tissue by movement of the outer needle.

The present invention economically and conveniently provides biopsy-marker assemblies for marking a biopsy sample site and obtaining a biopsy sample. Biopsy devices can be pre-loaded with a marker for automatic marking of the biopsy site. Using the present invention biopsy and biopsy sites marking occurs simultaneously without the need for complex additional steps. Biopsy sites can then be later located and accessed surgically as necessary.

While the invention has been illustrated and described in detail in the drawings and foregoing description, the same is to be considered as illustrative and not restrictive in character. It should be understood that only the preferred embodiments have been shown and described and that all changes and modifications that come within the spirit of the invention are desired to be protected.

What is claimed:

1. A biopsy-marking assembly for obtaining a biopsy sample from a biopsy site in a patient and marking the biopsy site, comprising:

an outer hollow needle defining a lumen therethrough;

an inner needle defining a first end having a tissue cutting point and a cavity adjacent said first end for receiving a tissue sample, said inner needle slidingly engaged within said lumen, said inner needle slideable relative to said outer needle between a first position wherein said first end of said inner needle is retracted within said lumen so that said outer needle covers said cavity and a second position wherein said first end of said inner needle is extended away from said outer needle to expose said cavity to tissue in the biopsy site;

firing means for moving said inner needle and said outer needle with respect to each other; and marking means for marking the biopsy site before a biopsy sample is taken at the site.

2. The assembly of claim 1 wherein said marking means is carried in said cavity when said inner needle is in the first position.

3. A biopsy-marking assembly for obtaining a biopsy sample from a biopsy site in a patient and marking the biopsy site, comprising:

an outer hollow needle defining a lumen therethrough;

an inner needle defining a first end having a tissue cutting point and a cavity adjacent said first end for receiving a tissue sample, said inner needle slidingly engaged within said lumen, said inner needle being slideable relative to said outer needle between a first position wherein said first end of said inner needle is retracted within said lumen so that said outer needle covers said cavity and a second position wherein said first end of said inner needle is extended away from said outer needle to expose said cavity to tissue in the biopsy site;

firing means for moving said inner needle and said outer needle with respect to each other; and a marking element contained within said cavity when said inner needle is in the first position.

4. The assembly of claim 3, wherein said marking element is a micro-coil.

5. The assembly of claim 3, wherein said marking element is a metal rod.

6. The assembly of claim 5, wherein said rod is spring-coiled within said cavity when said inner needle is in the first position.

7. The assembly of claim 5, wherein said rod includes two legs and a joint between said two legs, said rod folded with said two legs facing one another and compressed within said cavity when said inner needle is in the first position.

8. The assembly of claim 5, wherein said rod is a continuous oval.

9. The assembly of claim 8, wherein said rod is compressed within said cavity when the inner needle is in the first position.

10. The assembly of claim 5 wherein said rod is coiled and compressible into said cavity when the inner needle is in the first position.

11. The assembly of claim 5 wherein said rod includes a pair of opposite ends and a curved middle portion which forms a spring when said rod is compressed within said cavity when said inner needle is in the first position.

12. The assembly of claim 3 wherein said marking element is composed of a shape memory alloy.

13. The assembly of claim 12 wherein said marking element comprises a first leg, a second leg and a joint disposed between said legs, said marker having a first marker position with said first leg and said second leg forced away from one another and a second released position wherein said legs and said joint form a V, the marker having a shape and size configured to be received within a cavity of a biopsy needle for transport to a biopsy site.

14. The assembly of claim 3 wherein said marking element includes stabilization means for grasping tissue.

15. The assembly of claim 14 wherein said stabilization means includes surface projections.

16. A biopsy-marking assembly for obtaining a biopsy sample from a biopsy site in a patient and marking the biopsy site, comprising a hollow needle defining a cavity for receiving a tissue sample;

cutting means for cutting tissue and collecting the tissue in the cavity; and marking means for marking the biopsy site before a biopsy sample is taken at the site.

17. A biopsy-marking assembly for obtaining a biopsy sample from a biopsy site in a patient and marking the biopsy site, comprising a hollow needle defining a cavity for receiving a tissue sample;

cutting means for cutting tissue and collecting the tissue in the cavity; and a marking element contained with said cavity for delivery to the biopsy site.

18. A method for obtaining a biopsy sample and marking the biopsy site, comprising:

providing a biopsy device, the device having,
an outer hollow needle defining a lumen therethrough;
an inner needle defining a first end having a tissue cutting point and said inner needle defining a cavity adjacent said first end for receiving a tissue sample, said inner needle slidingly engaged within said lumen,
said inner needle slideable relative to said outer needle between a first position wherein said first end of said inner needle is retracted within said lumen so that said outer needle covers said cavity and a second position wherein said first end of said inner needle is extended away from said outer needle to expose said cavity to tissue in the biopsy site, and
means for moving said inner needle and said outer needle with respect to each other;

loading the cavity with a marker element and placing the inner needle in the first position to obtain a biopsy-marker assembly;

inserting the biopsy-marker assembly into the patient so that the point is adjacent the biopsy site;

moving the inner needle to expose the cavity to tissue and deposit the marker element in the biopsy site;

sliding the outer needle over the inner needle to trap a tissue sample within the cavity after depositing the marker element; and withdrawing the biopsy device with the sample trapped within the cavity and the marker deposited at the biopsy site.

19. The method of claim 18, further comprising:

rotating the inner needle after depositing the marker element and before sliding the outer needle.

20. A method for obtaining a biopsy sample and marking the biopsy site, comprising:

providing a biopsy-marker assembly, the assembly having,
an outer hollow needle defining a lumen therethrough;
an inner needle defining a first end having a tissue cutting point and said inner needle defining a cavity adjacent said first end for receiving a tissue sample, said inner needle slidingly engaged within said lumen,
said inner needle slideable relative to said outer needle between a first position wherein said first end of said inner needle is retracted within said lumen so that said outer needle covers said cavity and a second position wherein said first end of said inner needle is extended away from said outer needle to expose said cavity to tissue in the biopsy site,
means for moving said inner needle and said outer needle with respect to each other and
a marker element disposed within the cavity;

inserting the biopsy-marker assembly into the patient so that the point is adjacent the biopsy site;

moving the inner needle to expose the cavity to tissue and deposit the marker element in the biopsy site;

sliding the outer needle over the inner needle to trap a tissue sample within the cavity after depositing the marker element; and withdrawing the biopsy device with the sample trapped within the cavity and the marker deposited at the biopsy site.

21. The method of claim 20, further comprising:

rotating the inner needle after depositing the marker element and before sliding the outer needle.

* * * * *